(12) United States Patent
Cruise et al.

(10) Patent No.: US 11,744,925 B2
(45) Date of Patent: Sep. 5, 2023

(54) COATINGS

(71) Applicant: MicroVention, Inc., Aliso Viejo, CA (US)

(72) Inventors: Gregory M. Cruise, Rancho Santa Margarita, CA (US); Steve Plotkin, Beaumont, CA (US); Emily Hsu, Irvine, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 535 days.

(21) Appl. No.: 16/773,685

(22) Filed: Jan. 27, 2020

(65) Prior Publication Data

US 2020/0237970 A1 Jul. 30, 2020

Related U.S. Application Data

(60) Provisional application No. 62/797,853, filed on Jan. 28, 2019.

(51) Int. Cl.
| | |
|---|---|
| *C09D 133/14* | (2006.01) |
| *A61L 29/04* | (2006.01) |
| *A61L 29/08* | (2006.01) |
| *C09D 135/02* | (2006.01) |
| *B05D 3/06* | (2006.01) |
| *B05D 7/00* | (2006.01) |

(52) U.S. Cl.
CPC ........... *A61L 29/085* (2013.01); *A61L 29/041* (2013.01); *B05D 3/067* (2013.01); *B05D 7/546* (2013.01); *C09D 133/14* (2013.01); *C09D 135/02* (2013.01); *A61L 2300/452* (2013.01); *A61L 2400/10* (2013.01); *A61L 2420/02* (2013.01); *A61L 2420/08* (2013.01)

(58) Field of Classification Search
CPC .. C09D 133/14; C09D 135/02; A61L 2400/10
See application file for complete search history.

(56) References Cited

U.S. PATENT DOCUMENTS

| | | | |
|---|---|---|---|
| 2006/0121217 A1* | 6/2006 | Childs ................ | B01D 67/0088 428/34.1 |
| 2009/0324666 A1* | 12/2009 | Krongauz ............... | A61L 27/54 424/409 |
| 2010/0198168 A1* | 8/2010 | Rooijmans ............ | A61L 29/085 522/18 |
| 2011/0151000 A1* | 6/2011 | Schultz ................... | A61L 31/16 424/490 |
| 2011/0183867 A1* | 7/2011 | Davies ................... | B82Y 30/00 506/10 |
| 2018/0325649 A1* | 11/2018 | Wu ......................... | A61L 31/14 |

FOREIGN PATENT DOCUMENTS

| | | |
|---|---|---|
| WO | 2008/104573 A2 | 9/2008 |
| WO | 2020/159881 A1 | 8/2020 |

OTHER PUBLICATIONS

International Search Report and Written Opinion, dated Apr. 14, 2020, for International Application No. PCT/US2020/015240 filed on Jan. 27, 2020.
Nagaoka et al.. Low friction hydrophilic surface for medical devices. Journal of Bioactive and Compatible Polymers, 5:212-226 (1990).

* cited by examiner

*Primary Examiner* — Cachet I Proctor
(74) *Attorney, Agent, or Firm* — K&L Gates LLP; Brian J. Novak; Benjamin D. Heuberger

(57) ABSTRACT

Lubricious coatings for medical devices and their uses are described.

19 Claims, No Drawings

COATINGS

RELATED APPLICATIONS

This application claims priority of U.S. Provisional Patent Application No. 62/797,853, filed Jan. 28, 2019, the entire content of which is incorporated herein by reference.

FIELD

Described herein are coatings for medical devices and methods of applying those coatings.

BACKGROUND

Catheters and microcatheters are tubular devices that are used to conduct diagnostic and therapeutic endovascular interventions. Catheters are often formed of thermoplastic polymers that have high frictional forces. These high frictional forces make vascular navigation difficult. Providing a coated catheter or microcatheter with a lubricious coating as described herein would be useful and beneficial.

SUMMARY

There herein described coatings can be applied to medical devices such as medical devices that can be subjected to human tissues. In some embodiments, the coatings can be applied to medical devices can are used inside vessels or other lumens. In some embodiments, the vessels can be blood vessels. In some embodiments, the medical devices can be catheters or microcatheters.

The coatings can be synthetic and durable and lubricious. In some embodiments, the coatings can be ultra-violet (UV) cured. Lubricious coatings can reduce and/or minimize frictional forces between a medical device, such as a catheter or microcatheter, and a vessel wall, thereby enhancing trackability of the medical device throughout the vasculature. The surfaces of catheters are modified with lubricious coatings to reduce the frictional forces and enhance the ability of the catheter to be advanced through tortuous and distal vasculature.

In some embodiments, the herein described coating can include two layers, a base coat and a top coat. The base coat functions as a tie layer between the catheter's thermoplastic polymer surface and the top coat. The base coat is designed to adhere to the catheter and provide binding sites for the attachment of the top coat. The top coat is designed to adhere to the base coat and provide lubricity to reduce the frictional forces when the catheter is moved in the vasculature.

The coatings can generally include: a base coat including a copolymer of a first tetrahydrofurfuryl acrylate monomer and a second monomer including a functional group amenable to further derivatization and plurality of reactive moieties, and a top coat including a hydrophilic polymer containing more than two reactive moieties per molecule.

The coatings can generally include: a base coat including a copolymer of a first tetrahydrofurfuryl acrylate monomer and a second monomer including a functional group amenable to further derivatization and plurality of reactive moieties, and a top coat including a hydrophilic polymer containing two or fewer (e.g., 2, 1, or 0, or less than two) reactive moieties per molecule.

Methods of coating a thermoplastic surface, such as a catheter or microcatheter surface, are also described. The methods can include: applying a base coat including a copolymer of a first tetrahydrofurfuryl acrylate monomer and a second monomer to the thermoplastic surface, and applying a top coat to the base coat, wherein the top coat includes a hydrophilic polymer.

DETAILED DESCRIPTION

Described herein are coatings for medical devices. In some embodiments, the coatings can increase the lubricity of the medical device. These medical devices can include catheters and microcatheters that are formed at least partially of thermoplastic polymers/materials. The thermoplastic polymers can include, but are not limited to, poly(olefins), poly(amides), poly(ethylene terephthalate), poly(urethanes), poly(ether sulfones), poly(carbonates), poly(vinyl chloride), copolymers thereof, and derivatives thereof. In some embodiments, the thermoplastic polymers can include, but are not limited to, poly(amides), poly(ethylene terephthalate), poly(urethanes), poly(ether sulfones), poly(carbonates), poly(vinyl chloride), copolymers thereof, and derivatives thereof.

These thermoplastic polymers can have high frictional forces. These high frictional forces make vascular navigation difficult. Thus, the herein described coatings can increase lubricity of the thermoplastic polymer surfaces. In some embodiments, the coatings can include a base coat and a top coat. The base coat functions as a tie layer between the catheter's thermoplastic polymer and the top coat. The base coat is designed to adhere to the catheter and provide binding sites for the attachment of the top coat. The top coat is designed to adhere to the base coat and provide lubricity to reduce the frictional forces when the catheter is moved in the vasculature.

In some embodiments, the base coat includes a polymer that is a copolymer of a first tetrahydrofurfuryl acrylate monomer and at least one other monomer with functional groups capable of further chemical reaction such as hydroxyl, amine, and carboxylic acid groups. In some embodiments, the at least one other monomer including hydroxyl groups can be hydroxyethyl methacrylate, hydroxyethyl acrylate, hydroxypropyl acrylate, hydroxypropyl methacrylate, hydroxybutyl acrylate, hydroxybutyl methacrylate, combinations thereof, and derivatives thereof. In some embodiments, the at least one other monomer including amine groups can be N-(3-aminopropyl) methacrylamide, 2-aminoethyl methacrylate, 2-aminoethyl methacrylamide, combinations thereof, and derivatives thereof. In some embodiments, the at least one other monomer including carboxylic acids can be acrylic acid, methacrylic acid, beta-carboxyethyl acrylate, combinations thereof, and derivatives thereof.

To prepare the base coat copolymer, the two or more monomers and optionally an initiator can be dissolved in a solvent. The solvent can be any solvent that dissolves the two or more monomers and the optional initiator. Solvents can include benzene, toluene, xylene, dimethylformamide, dimethyl sulfoxide, dioxane, 2-methyltetrahydrofuran, anisole, benzonitrile, chlorinated aromatic solvents, diisopropyl ether, diglyme, butanol, and combinations thereof.

Initiators can be used to start the polymerization of the monomers in the solution. The polymerization can be initiated by reduction-oxidation, radiation, heat, or any other method known in the art. Radiation cross-linking of the monomers in solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomers in solution.

In some embodiments, the initiator is azobisisobutyronitrile (AIBN) or a water soluble AIBN derivatives (2,2'-azobis(2-methylpropionamidine) dihydrochloride), or 4,4'-azobis(4-cyanopentanoic acid). Other initiators can include N,N,N',N'-tetramethylethylenediamine, ammonium persulfate, benzoyl peroxides, and combinations thereof, including azobisisobutyronitriles.

In some embodiments, the initiator concentration can be from about 0.25% w/w to about 2% w/w of the mass of the monomers in solution.

In some embodiments, the polymerization reaction can be performed at elevated temperatures, such as in the range from about 65° C. to about 85° C.

After the polymerization is completed, the copolymer can be recovered by precipitation in a non-solvent and dried under vacuum.

The resulting copolymer can have a molecular weight between about 15,000 g/mole and about 150,000 g/mole or between 25,000 g/mole to 100,000 g/mole. This molecular weight can be derived by gel permeation chromatography with poly(styrene) or poly(methyl methacrylate) molecular weight standards.

Following polymerization, reactive groups, such as acrylates and/or methacrylates, are added to the copolymer via the hydroxyl, amine, and/or carboxylic acid groups of the second or more monomers. In general, the derivatization compound is a hetero-bifunctional compound. One moiety reacts with the hydroxyl, amine, and/or carboxylic acid groups of the copolymer. The other moiety is an acrylate or methacrylate group. Suitable derivatization compounds include 2-isocyanatoethyl acrylate, 2-isocyanatoethyl methacrylate, acrylic acid N-hydroxysuccinimide ester, methacrylic acid N-hydroxysuccinimide ester, hetero-bifunctional poly(ethylene glycol) with acrylate and isocyanate groups, combinations thereof, and derivatives thereof.

To prepare the derivatized copolymer, the copolymer, and derivatization compound, and optionally any catalyst, can be dissolved in a solvent. In general, any solvent that dissolves the components can be used. Solvents can include dimethyl formamide, dimethyl sulfoxide, toluene, acetone, acetonitrile, N,N-dimethylacetamide, N-methyl-2-pyrrolidone, and combinations thereof.

When reacting a derivatization with a nucleophilic group of the base coat copolymer, the molar equivalent of derivatization agent can range from about 5% to about 80% or about 10% to about 50% of the available nucleophilic groups. This level of derivatization corresponds to a range of 4 to 50 reactive groups per molecule. Further, in some embodiments, a Lewis base can be added of as a catalyst. Lewis bases can include triethylamine and pyridine. The Lewis base can be provided at a concentration of about 1% to about 10% of the moles of the derivatization compound added.

The reaction can proceed at elevated temperatures, such as about 45° C. to form the base coat. After the derivatization is complete, the completed, decorated copolymer can be recovered by precipitation in a non-solvent and dried under vacuum. In some embodiments, the reaction can proceed at ambient temperatures (e.g., 15-25, e.g., 20° C.).

The top coat can be formed atop the base coat. The top coat polymer can include a core, hydrophilic polymer that is derivatized with polymerizable groups. The core hydrophilic polymer can be any naturally-occurring or synthetic polymer, derivatives thereof and combinations thereof. In some embodiments, the core hydrophilic polymer is at least to some degree, soluble in water.

The structure of the core hydrophilic polymer can be linear or branched, including graft, star, comb, brush, and dendrimer structures.

In some embodiments, the core hydrophilic polymer includes Formula (I), which includes two or more hydroxyl moieties, which may serve as points of attachment for additional moieties, including, for example, ethylenically unsaturated groups including acrylates, methacrylates, acrylamides, methacrylamides, combinations thereof, and derivatives thereof. In some embodiments, the core hydrophilic polymer includes Formula (I), which includes four hydroxyl moieties, which may serve as points of attachment for the additional moieties. In some embodiments, the core hydrophilic polymer includes Formula (I), which includes eight hydroxyl moieties, which may serve as points of attachment for the additional moieties. In some embodiments, each of the hydroxyls of the core hydrophilic polymer may be functionalized with an ethylenically unsaturated moiety. In some embodiments, the resulting molecule (Formula II), when there is a plurality of such molecules, includes an average of less than two ethylenically unsaturated moieties per molecule. In some embodiments, the plurality of molecules includes an average of about 1.2 to 1.6 reactive moieties per molecule. In some embodiments, the plurality of molecules includes two or fewer ethylenically unsaturated moieties per molecule and an average of about 1.0 to 1.9 moieties per molecule in the plurality.

In some embodiments, each molecule in the plurality of molecules includes two or fewer ethylenically unsaturated moieties and the plurality of molecules includes an average of about 0.01 to less than 2 moieties per molecule in the plurality.

In some embodiments, each molecule in the plurality of molecules includes two or fewer ethylenically unsaturated moieties and the plurality of molecules includes an average of about 0.1 to less than 2 moieties per molecule in the plurality.

In some embodiments, each molecule in the plurality of molecules includes two or fewer ethylenically unsaturated moieties and the plurality of molecules includes an average of about 0.3 to less than 2 moieties per molecule in the plurality.

In some embodiments, each molecule in the plurality of molecules includes two or fewer ethylenically unsaturated moieties and the plurality of molecules includes an average of about 0.6 to less than 2 moieties per molecule in the plurality.

In some embodiments, each molecule in the plurality of molecules includes two or fewer ethylenically unsaturated moieties and the plurality of molecules includes an average of about 0.9 to less than 2 moieties per molecule in the plurality.

In some embodiments, each molecule in the plurality of molecules includes two or fewer ethylenically unsaturated moieties and the plurality of molecules includes an average of about 1 to less than 2 moieties per molecule in the plurality.

In some embodiments, each molecule in the plurality of molecules includes two or fewer ethylenically unsaturated moieties and the plurality of molecules includes an average of about 0.1 to about 1 moieties per molecule in the plurality.

In some embodiments, each molecule in the plurality of molecules includes two or fewer ethylenically unsaturated moieties and the plurality of molecules includes an average of about 1.0 to about 1.8 moieties per molecule in the plurality.

In some embodiments, each molecule in the plurality of molecules includes two or fewer ethylenically unsaturated moieties and the plurality of molecules includes an average of about 1.2 to about 1.8 moieties per molecule in the plurality.

In some embodiments, each molecule in the plurality of molecules includes two or fewer ethylenically unsaturated moieties and the plurality of molecules includes an average of about 1.2 to about 1.6 moieties per molecule in the plurality.

Thus, in some embodiments, the resulting molecule includes a branched hydrophilic polymer with two or more arms, wherein each arm is a linear polymer and having 0, 1, or 2 ethylenically unsaturated moieties such that the molecule includes less than an average of two ethylenically unsaturated moieties and an average of about 1.2 to 1.6 (e.g., about 0.1-1.9, e.g. about 0.5-1.8, e.g., about 1.0-1.7, e.g., about 1.5-1.7) ethylenically unsaturated moieties per molecule when there is a plurality of such molecules.

Thus, in some embodiments, Formula I has a structure $Z-(OH)_n$, where n is two or more, and Z is a $C_{5-18}H_{8-30}O_{0-5}$ moiety. In some embodiments, n is 2-8. In some embodiments, n is 4-8. In some embodiments, n is 4. In some embodiments, n is 8. In some embodiments, Z is a $C_{15-18}H_{24-30}O_{2-5}$ moiety. In some embodiments, Z is a $C_{5-6}H_{8-10}O_{0-1}$ moiety. In some embodiments, Z is a $C_{18}H_{30}O_5$ moiety and n is 8. In some embodiments, Z is a $C_{15}H_{24}O_2$ moiety and n is 8. In some embodiments, Z is a $C_6H_{10}O$ moiety and n is 4. In some embodiments, Z is a $C_5H_8$ moiety and n is 4.

In some embodiments, Formula I is a hexaglycerol, tripentaerythritol, 3,3'-oxybis(propane-1,2-diol), or 2,2-bis(hydroxymethyl)propane-1,3-diol moiety.

In some embodiments, Formula I is a moiety selected from:

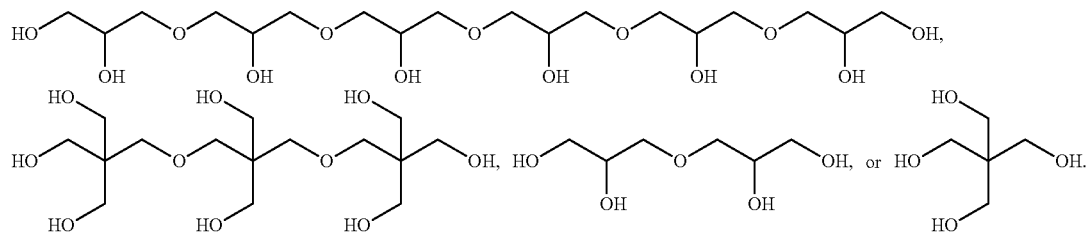

In some embodiments, Formula II has a structure $(Z-((OCH_2CH_2OH)_{n-j})-((OCH_2CH_2X)_j))$, wherein Z is defined as in Formula I, j is greater than 0 to less than 2, and X is an ethynically unsaturated group. In some embodiments, j is about 0.01 to less than 2. In some embodiments, j is about 0.1 to less than 2. In some embodiments, j is about 0.3 to less than 2. In some embodiments, j is about 0.6 to less than 2. In some embodiments, j is about 0.9 to less than 2. In some embodiments, j is about 1.0 to less than 2. In some embodiments, j is about 0.01 to about 1.0. In some embodiments, j is about 0.1 to about 1.0. In some embodiments, j is about 1.2 to about 1.8. In some embodiments, j is about 1.2 to about 1.6. In some embodiments, j is about 1.4 to about 1.5. In some embodiments, the ethynically unsaturated group is independently selected from acrylates, methacrylates, acrylamides, methacrylamides, combinations thereof, or derivatives thereof. In some embodiments, the ethynically unsaturated group is independently selected from an acrylate, a methacrylate, an acrylamide, or a methacrylamide.

Polymer used for the top coat can include, but are not limited to naturally-occurring polymers such as proteins, collagen, albumin, fibrin, elastin, polypeptides, oligonucleotides, polysaccharides, hyaluronic acid, gelatin, chitosan, alginate, cellulose, carboxymethyl cellulose, hydroxymethyl cellulose, hydroxypropyl cellulose, and dextran.

Polymer used for the top coat can include, but are not limited to synthetic polymers such as poly(ethers), poly(ethylene glycol), poly(ethylene oxide), poly(propylene glycol), poly(lactams), poly(vinylpyrrolidone), poly(acrylates), poly(urethanes), poly(anhydrides), poly(amino acids), poly(carboxylic acids), poly(amides), poly(vinyl alcohol), and poly(phosphazenes).

Molecular weights of the hydrophilic polymers can range from about 500 amu to about 100,000 amu or from about 1,000 amu to about 40,000 amu.

Reactive groups, such as, but not limited to acrylates and/or methacrylates, can be added to the polymer via any convenient reactive moiety, such as hydroxyls, amines, or carboxylic acids, with a derivatization compound. In some embodiments, the derivatization compound can be a hetero-bifunctional compound. One moiety can react with the hydroxyl, amine, and/or carboxylic acid groups of the copolymer. The other moiety can be an acrylate or methacrylate group.

In some embodiments, the derivatization compound can include acryloyl chloride, methacryloyl chloride, 2-isocyanatoethyl acrylate, 2-isocyanatoethyl methacrylate, acrylic acid N-hydroxysuccinimide ester, methacrylic acid N-hydroxysuccinimide ester, hetero-bifunctional poly(ethylene glycol) with acrylate and isocyanate groups, combinations thereof, and derivatives thereof.

To prepare the derivatized polymer, the polymer, derivatization compound, and the optional catalyst are dissolved in a solvent. In general, any solvent that dissolves the top coat polymer, derivatization agent, and the optional catalyst can be used. Solvents can include aromatic and chlorinated solvents, including benzene, toluene, xylene, dichloromethane, chloroform, and combinations thereof.

When reacting a derivatization agent with a reactive moiety of the top coat polymer, the target derivatization corresponds to less than two groups per molecule. Additionally, in some embodiments, the derivatization can include addition of a Lewis base as a catalyst. In some embodiments, the Lewis base can be triethylamine and pyridine, in a concentration of about 1% to about 10% of the moles of the derivatization compound added.

In some embodiments, the derivatization reaction proceeds at room temperature.

After the derivatization is complete, an activated polymer can be recovered by precipitation in a non-solvent and dried under vacuum.

The base coat can be applied to a medical device surface, e.g., a thermoplastic material. The catheter is first cleaned by a solvent wipe to remove any gross contamination from its surface. In some embodiments, the catheter is wiped with a solvent. In some embodiments, any solvent can be used if it does not dissolve or degrade the thermoplastic material of the catheter. Solvents can include glycol ethers, methyl ethyl ketone, chlorinated solvents, tetrahydrofuran, hexane, ethyl acetate and acetone.

Following solvent cleaning, in some embodiments, the catheter shaft can be plasma treated to further clean its surface. In some embodiments, the catheter is not plasma treated. Plasmas derived from various gases can be used. In some embodiments, the plasma gases can be argon and oxygen. In some embodiments, both argon and oxygen plasmas can be used.

The base coat solution can include the solvent, base coat copolymer, an optional initiator, and an optional surfactant. Generally, any solvent or mixtures of solvents may be utilized, provided that the components can be dissolved into the solvent or solvent mixtures. Solvents can include water, alcohols, glycol ethers, aromatics, polar aprotic solvents, and combinations thereof. In some embodiments, the solvent can include methanol, ethanol, isopropyl alcohol, 2-ethoxy ethanol, propylene glycol monomethyl ether acetate, benzene, toluene, xylene, dimethyl formamide, dimethyl sulfoxide, and combinations thereof.

The base coat copolymer can be dissolved into the solvent at a concentration ranging from about 0.2% w/w to about 35% w/w, about 0.2% w/w to about 40% w/w, about 0.2% w/w to about 50% w/w, about 0.5% w/w to about 35% w/w, about 0.5% w/w to about 40% w/w, about 0.5% w/w to about 50% w/w, about 1% w/w to about 35% w/w, about 1% w/w to about 40% w/w, or about 1 w/w to about 50% w/w, depending on the desired viscosity of the basecoat solution. In some embodiments, the base coat copolymer concentration is about 15% w/w.

In some embodiments, if included, initiators can include Norrish Type I initiators, Norrish Type II initiators, and combinations thereof. Norrish Type I or free-radical photo-initiators can include benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, or a combination thereof. In some embodiments, Norrish Type I photoinitiators can include Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenyl-propan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly{2-hydroxy-2-methyl-1-[4-(1-methylvinyl)phenyl]propan-1-one}, Fratelli Lamberti), Esacure KIP 100 F (blend of poly{2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly{2-hydroxy-2-methyl-1-[4-(1-methylvinyl)phenyl]propan-1-one}, 2,4,6-trimethylbenzoyldiphenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis(2,4,6-trimethylbenzoyl)-phenyl-phosphine-oxide, Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-1-one, Ciba-Geigy), or a combination thereof.

In some embodiments, mixtures of type I photo-initiators can be used.

Norrish Type II photo-initiators can also be used in the base coat formulation. These initiators can include aromatic ketones such as benzophenone, xanthone, derivatives of benzophenone (e.g. chlorobenzophenone), blends of benzophenone and benzophenone derivatives (e.g. Photocure 81, a 50/50 blend of 4-methyl-benzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations of these photoinitiators.

In some embodiments, the base coat formulation can include combinations of Norrish Type I and Norrish Type II initiators.

The initiator concentration in the solvent can range from about 0.1% to about 6% w/w. In some embodiments, initiator concentration in the solvent can be about 0.6% w/w.

The base coat solution may also optionally include a surfactant. In some embodiments, any surfactant may be used. Surfactants can include sodium lauryl sulfate, Tween 20, Span 80, Triton X-100, Pluronic F68, Pluronic L-81, combinations thereof, and derivatives thereof. The optional surfactant can be dissolved into the selected solvent at a concentration ranging from about 0.1% w/w to about 15% w/w. In some embodiments, the surfactant concentration is about 0.8% w/w.

In some embodiments, to apply the base coat to a catheter, the length of the catheter desired to be coated is inserted into the base coat solution. The dip time, or amount of time the catheter spends in the base coat solution, ranges from about 0.2 to about 10 minutes, about 0.5 to about 10 minutes, about 2 to about 8 minutes, about 3 to about 6 minutes, or about 0.5 to about 8 minutes. In some embodiments, the dip time can be about 5 minutes.

In some embodiments, to apply the base coat to a catheter, the length of the catheter desired to be coated is inserted into the base coat solution. The dip time, or amount of time the catheter spends in the base coat solution, ranges from about 0.2 seconds to about 10 minutes, about 1 second to about 10 minutes, about 2 seconds to about 8 minutes, about 3 seconds to about 6 minutes, or about 0.5 seconds to about 8 minutes.

In some embodiments, to apply the base coat to a catheter, the length of the catheter desired to be coated is inserted into the base coat solution. The dip time, or amount of time the catheter spends in the base coat solution, ranges from about 0.2 seconds to about 10 seconds, about 1 second to about 10 seconds, about 2 seconds to about 8 seconds, about 3 seconds to about 6 seconds, or about 0.5 seconds to about 8 seconds. In some embodiments, the dip time can be about 5 seconds.

In other embodiments, the base coat can be applied by spraying, brushing, spin coating, or the like, or a combination thereof including or not including dip coating.

In some embodiments, only portions of the catheter are coated. Therein portions of the catheter can be masked so that base coat is not applied to the masked regions.

After dip coating or otherwise applying the base coat, the catheter is exposed to ultraviolet radiation with a wavelength ranging from about 10 nm to about 400 nm, about 100 nm to about 400 nm, about 200 nm to about 400 nm, about 200 nm to about 300 nm, or about 300 nm to about 400 nm. Combinations of wavelengths in this range can also provide a suitable base coat. In one embodiment, ultraviolet radiation can be applied by a first wavelength between about 200 nm to about 300 nm and a second wavelength between about 300 nm to about 400 nm. In one embodiment, wavelengths can include 254 and 365 nm.

The cure time, or amount of time the catheter is exposed to ultraviolet radiation, ranges from about 0.5 to about 10 minutes, about 1 to about 10 minutes, about 1 to about 8 minutes, about 0.5 to about 6 minutes, about 1 to about 6 minutes, about 1 to about 3 minutes, or about 0.5 to about 30 minutes. In one embodiment, the cure time is about 2 minutes.

The cure time, or amount of time the catheter is exposed to ultraviolet radiation, ranges from about 0.5 seconds to about 10 minutes, about 1 second to about 10 minutes, about 1 second to about 8 minutes, about 0.5 seconds to about 6 minutes, about 1 second to about 6 minutes, about 1 second to about 3 minutes, or about 0.5 seconds to about 30 minutes.

The cure time, or amount of time the catheter is exposed to ultraviolet radiation, ranges from about 0.5 seconds to about 10 seconds, about 1 second to about 10 seconds, about 1 second to about 8 seconds, about 0.5 seconds to about 6 seconds, about 1 second to about 6 seconds, about 1 second to about 3 seconds, or about 0.5 seconds to about 30 seconds. In one embodiment, the cure time is about 30 seconds.

In some embodiments, the base coat application process is complete after the completion of the cure time.

The top coat can be applied to a completed base coat. The top coat solution can include the solvent, a top coat polymer, an optional initiator, and an optional surfactant. In general, any solvent or mixtures of solvents may be utilized, provided that the components can be dissolved into the solvent or solvent mixtures. Suitable solvents can include water, alcohols, glycol ethers, aromatics, polar aprotic solvents, and combinations thereof. In some embodiments, the solvent can include methanol, ethanol, isopropyl alcohol, 2-ethoxy ethanol, propylene glycol monomethyl ether acetate, benzene, toluene, xylene, dimethyl formamide, dimethyl sulfoxide, and combinations thereof.

The top coat polymer can be dissolved into the selected solvent at a concentration ranging from about 5% w/w to about 75% w/w, about 5% w/w to about 80% w/w, about 5% w/w to about 90% w/w, about 10% w/w to about 80% w/w, about 10% w/w to about 75% w/w, about 5% w/w to about 50% w/w, about 5% w/w to about 40% w/w, about 5% w/w to about 40% w/w, about 20% w/w to about 40% w/w, about 20% w/w to about 30% w/w, depending on the desired viscosity of the top coat solution. In one embodiment, the top coat polymer concentration is about 25% w/w.

The optional initiator can include Norrish Type I initiators, Norrish Type II initiators, and combinations thereof. Norrish Type I or free-radical photo-initiators can include benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Norrish Type I photoinitiators can include Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenylpropan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly {2-hydroxy-2-methyl-1-[4-(1-methylvinyl)phenyl]propan-1-one}, Fratelli Lamberti), Esacure KIP 100 F (blend of poly {2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly {2-hydroxy-2-methyl-1-[4-(1-methylvinyl)phenyl]propan-1-one}, 2,4,6-trimethylbenzoyldiphenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis(2,4,6-trimethylbenzoyl)-phenyl-phosphine-oxide, Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-1-one, Ciba-Geigy), and the like. Also, mixtures of type I photo-initiators can be used.

Norrish Type II photo-initiators that can be used include aromatic ketones such as benzophenone, xanthone, derivatives of benzophenone (e.g. chlorobenzophenone), blends of benzophenone and benzophenone derivatives (e.g. Photocure 81, a 50/50 blend of 4-methyl-benzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations thereof.

In some embodiments, the top coat formulation can include combinations of Norrish Type I and Norrish Type II initiators.

The initiator concentration in the solvent can range from about 0.1% to about 6% w/w. In some embodiments, initiator concentration in the solvent can be about 0.5% w/w.

The top coat solution may also contain a surfactant. In general, any surfactant may be used. In some embodiments, surfactants can include sodium lauryl sulfate, Tween 20, Span 80, Triton X-100, Pluronic F68, Pluronic L-81, combinations thereof, and derivatives thereof. The optional surfactant can be dissolved into the selected solvent at a concentration ranging from about 0.1% w/w to about 5% w/w. In some embodiments, the surfactant concentration is about 0.6% w/w.

In some embodiments, to apply the top coat to a base coated catheter, the length of the catheter desired to be coated is inserted into the top coat solution. The dip time, or amount of time the catheter spends in the top coat solution, ranges from about 0.2 to about 20 minutes, about 0.5 to about 20 minutes, about 2 to about 15 minutes, about 3 to about 15 minutes, or about 8 to about 12 minutes. In some embodiments, the dip time can be about 10 minutes.

In some embodiments, the dip time, or amount of time the catheter spends in the top coat solution, ranges from about 0.2 seconds to about 20 minutes, about 0.5 seconds to about 20 minutes, about 2 seconds to about 15 minutes, about 3 seconds to about 15 minutes, or about 8 seconds to about 12 minutes.

In some embodiments, the dip time, or amount of time the catheter spends in the top coat solution, ranges from about 0.2 seconds to about 20 seconds, about 0.5 seconds to about 20 seconds, about 2 seconds to about 15 seconds, about 3 seconds to about 15 seconds, or about 8 seconds to about 12 seconds. In some embodiments, the dip time can be about 5 seconds.

In other embodiments, the top coat can be applied by spraying, brushing, spin coating, or the like, or a combination thereof including or not including dip coating.

In some embodiments, only portions of the catheter are coated with the top coat. Therein portions of the catheter can be masked so that top coat is not applied to the surface under the masked regions.

After dip coating or otherwise applying the top coat, the catheter is exposed to ultraviolet radiation with a wavelength ranging from about 10 nm to about 400 nm, about 100 nm to about 400 nm, about 200 nm to about 400 nm, about 200 nm to about 300 nm, or about 300 nm to about 400 nm. Combinations of wavelengths in this range can also provide a suitable base coat. In one embodiment, ultraviolet radiation can be applied by a first wavelength between about 200 nm to about 300 nm and a second wavelength between about 300 nm to about 400 nm. In one embodiment, wavelengths can include 254 and 365 nm.

The top coat cure time, or amount of time the catheter is exposed to ultraviolet radiation, ranges from about 0.5 to about 4 minutes, about 1 to about 4 minutes, about 1 to about 3 minutes, about 0.5 to about 3 minutes, about 1 to about 5 minutes, about 0.5 to about 3 minutes, or about 0.5 to about 50 minutes. In one embodiment, the cure time is about 2 minutes.

In some embodiments, the top coat cure time, or amount of time the catheter is exposed to ultraviolet radiation, ranges from about 0.5 to about 10 minutes, about 1 to about 10 minutes, about 1 to about 8 minutes, about 0.5 to about 8 minutes, about 1 to about 8 minutes, about 0.5 to about 8 minutes, or about 0.5 to about 50 minutes. In one embodiment, the cure time is about 5 minutes.

The herein described coatings can provide a reduction in maximum dynamic friction force [gf] when compared to an uncoated device. In some embodiments, the coatings can reduce the maximum dynamic friction force by about 50% or more. In other embodiments, the coatings can reduce the maximum dynamic friction force by about 75% or more. In other embodiments, the coatings can reduce the maximum dynamic friction force by about 95% or more. In other embodiments, the coatings can reduce the maximum dynamic friction force by about 75% to about 99%, e.g., about 80%-99%, about 85%-99%, about 90%-99%, about 91%, 92%, 93%, 94%, 95%, 96%, 97%, 98%, or 99%.

The herein described coatings can provide a reduction in average dynamic friction force at 60 mm displacement for 100 cycles [gf] when compared to an uncoated device. In some embodiments, the coatings can reduce the maximum dynamic friction force by about 50%. In other embodiments, the coatings can reduce the maximum dynamic friction force by about 75%. In other embodiments, the coatings can reduce the maximum dynamic friction force by about 95% or more. In other embodiments, the coatings can reduce the maximum dynamic friction force by about 75% to about 99%, e.g., about 80%-99%, about 85%-99%, about 90%-99%, about 91%, 92%, 93%, 94%, 95%, 96%, 97%, 98%, or 99%.

The herein described coatings can provide an increase in lubricity when compared to an uncoated device. In some embodiments, the coatings can increase the lubricity by about 50%. In other embodiments, the coatings can increase the lubricity by about 75%. In other embodiments, the coatings can increase the lubricity by about 95% or more. In other embodiments, the coatings can increase the lubricity by about 75% to about 99%, e.g., about 80%-99%, about 85%-99%, about 90%-99%, about 91%, 92%, 93%, 94%, 95%, 96%, 97%, 98%, or 99%.

EXAMPLE 1

Preparation of a Base Coat Polymer

To a 1 L round bottom flask are added 80.0 g of tetrahydrofurfuryl acrylate, 18.5 g of 4-hydroxybutyl acrylate and 250 mL of toluene. The solution is de-gassed by purging argon gas through for 30 min. Then, 1.0 gram AIBN initiator is added, and the mixture is purged with argon for another 10 min. The flask is immersed in an 80° C. oil bath and reflux condenser with argon inlet attached. The mixture is heated for 16 hours under argon. The reaction is cooled down and precipitated with 1.2 L of cold MTBE, precipitated product—viscous polymer is collected and dried at vacuum. Typical yield is 85-95%.

The dried polymer is dissolved in dry DMF (200 mL, about 0.5 g/mL) and treated with 0.84 mL of triethylamine and 3.0 mL of isocyanatoethyl acrylate. The mixture is stirred at ambient conditions for 16 hrs. The polymer is precipitated out with 0.8 L of water. The polymer is redissolved in 0.2 L acetone and precipitated in 0.8 L water, washed 2×300 mL of water and dried at high vacuum.

EXAMPLE 2

Preparation of a Liquid Base Coat Solution

In an appropriate container, 300 g of polymer from example 1 is dissolved in 2,000 mL of propylene glycol monomethyl ether acetate. Then 15 g of Pluronic L-81, 6 g 1-hydroxycyclohexyl phenyl ketone, and 6 g benzophenone are added. Complete dissolution is achieved with shaking for 30 minutes producing a clear, homogeneous solution.

EXAMPLE 3

Preparation of a Top Coat Macromer

Fifty (50) grams of PEG (Mw 4,000) is dried by azeotropic distillation with toluene. A solution of PEG in 250 mL of toluene is treated with 30 mL of dichloromethane, followed by addition of 7.0 mL of triethylamine and 4.04 mL of acryloyl chloride. The reaction mixture is stirred for 5 hrs and then precipitated salts are filtered off and top coat macromer is isolated by precipitation from 1 L of cold MTBE. Solids are separated by filtration, washed with additional 200 mL of MTBE and dried at high vacuum overnight.

EXAMPLE 4

Preparation of a Top Coat Macromer

Fifty (50) grams of 8-Arm PEG (Mw 20,000) is dried by azeotropic distillation with toluene. A solution of PEG in 250 mL of toluene is treated with 30 mL of dichloromethane, followed by addition of 0.46 mL of triethylamine and 0.25 mL of acryloyl chloride. The reaction mixture is stirred for 16 hrs and then precipitated salts are filtered off and top coat macromer is isolated by precipitation from 1.2 L of cold MTBE. Solids are separated by filtration, washed with additional 200 mL of MTBE and dried at high vacuum overnight.

EXAMPLE 5

Preparation of a Top Coat Solution

In a container, 9.0 g of polyethylene glycol di-acrylate (4,000 Mw) prepared in Example 3 is dissolved in 45.0 mL of methanol with shaking. Then, 0.23 g of Pluronic L-81 surfactant, 90 mg of benzophenone, and 90 mg of 1-hydroxycyclohexyl phenyl ketone are added. Complete dissolution with heating at 55° C. for 2 minutes results in a clear, homogenous solution.

EXAMPLE 6

Preparation of a Top Coat Solution

In a container, 400 g of polyethylene glycol acrylate (20 k Mw) prepared in example 4 is dissolved in 2,000 mL of methanol with shaking. Then, 10 g of Tween 80 surfactant, 4 g of benzophenone, and 4 g of 1-hydroxycyclohexyl phenyl ketone are added. Complete dissolution is achieved with shaking for 30 minutes producing a clear, homogeneous solution.

EXAMPLE 7

Coating a Microcatheter

A Harland PCX 175 Coating machine is charged with the basecoat and top coat solutions prepared in [0066] and [0069] respectively. A catheter with lengths of outer surface comprised of Grilamid L25 and Pebax 35D-72D durometer is prepared for coating by first wiping the outer surface with acetone. The catheter is then plasma treated with argon plasma (365 sccm, 300 watts, 500 mtorr) followed by oxygen plasma (120 sccm, 150 watts, 400 mtorr). The catheter is then affixed in the coating machine and coated using an automated, pre-programmed recipe. The sequential stepwise process dips the catheter in basecoat solution, extracts it at 5 cm/sec, UV cures the basecoat for 30 sec (365 nm λ, mJ/cm2 83.7 UV dose), dips the catheter in topcoat solution, extracts it at 0.6 cm/sec, and finally cures the top coat for 300 sec (365 nm λ, 837.0 mJ UV dose).

EXAMPLE 8

Lubricity

Microcatheter samples prepared in Example 7 are tested to evaluate lubricity using an Instron 5943 material tester equipped with a 5 N static load cell. A mechanical clamping fixture is attached to the load cell to hold the top of the microcatheter sample as its length is pulled through a hydraulic clamping fixture (clamping force of 1 lb.) submerged in a heated (37° C.) water bath containing distilled water. The test method cycles each sample repeatedly 20 times at a pull rate of 254 mm/min for 100 mm, with one cycle measured as starting at 0 mm displacement with the hydraulic clamp closed on the sample. Then, the sample is pulled through the hydraulic clamp for 100 mm displacement, and finally the hydraulic clamp is opened, and the sample is returned to 0 mm displacement. The maximum dynamic friction force and the average dynamic friction force at the 60 mm displacement mark is measured and presented in Table 1 below. Included in the table are lubricity measurement results for an uncoated sample run for 20 cycles as a comparison.

TABLE 1

| Sample Number | Maximum Dynamic Friction Force [gf] | Avg. Dynamic Friction Force at 60 mm Displacement [gf] |
| --- | --- | --- |
| 1 | 32.0 | 27.9 |
| 2 | 32.0 | 29.0 |
| Uncoated | 411 | 305 |

The coating of example 8 compared to an uncoated sample illustrates an increase in lubricity.

Although preferred embodiments have been described in this specification and the accompanying drawings, it will be appreciated that a number of variations and modifications may suggest themselves to those skilled in the pertinent arts. Thus, the scope of the present invention is not limited to the specific embodiments and examples described herein, but should be deemed to encompass alternative embodiments and equivalents.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A coating formulation comprising:
   a base coat including a copolymer of a first tetrahydrofurfuryl acrylate monomer and a second monomer including a functional group amenable to further derivatization and a plurality of reactive moieties, and
   a top coat including a hydrophilic polymer containing less than two reactive moieties per molecule.

2. The coating formulation of claim 1, wherein the copolymer has a molecular weight between about 15,000 g/mole and about 150,000 g/mole.

3. The coating formulation of claim 1, wherein the top coat is atop the base coat.

4. The coating formulation of claim 1, wherein the hydrophilic polymer is a protein, collagen, albumin, fibrin, elastin, polypeptide, oligonucleotide, polysaccharide, hyaluronic acid, gelatin, chitosan, alginate, cellulose, carboxymethyl cellulose, hydroxymethyl cellulose, hydroxypropyl cellulose, dextran, poly(ether), poly(ethylene glycol), poly(ethylene oxide), poly(propylene glycol), poly(lactam), poly(vinylpyrrolidone), poly(acrylate), poly(urethane), poly(anhydride), poly(amino acid), poly(carboxylic acid), poly(amide), poly(vinyl alcohol), poly(phosphazene), or a combination thereof.

5. The coating formulation of claim 1, wherein the hydrophilic polymer has a molecular weight between about 500 amu to about 100,000 amu.

6. The coating formulation of claim 1, providing about 50% or more increased lubricity to a device coated with the coating formulation as compared to the device prior to being coated with the coating formulation.

7. The coating formulation of claim 6, wherein the device is a catheter or microcatheter.

8. The coating formulation of claim 6, wherein the device is a medical device.

9. The coating formulation of claim 1, wherein the top coat comprises a hydrophilic polymer containing less than 1 reactive moieties per molecule.

10. The coating formulation of claim 1, wherein the second monomer is 4-hydroxybutyl acrylate, and the hydrophilic polymer containing less than two reactive moieties per molecule is a poly(ethylene glycol) containing less than two reactive moieties per molecule.

11. The coating formulation of claim 1, wherein the top coat consists essentially of a hydrophilic polymer containing less than two reactive moieties per molecule.

12. The coating formulation of claim 1, which reduces the maximum dynamic friction force by about 50% or more on a surface coated with the coating formulation as compared to the surface prior to being coated with the coating formulation.

13. The coating formulation of claim 1, which reduces the maximum dynamic friction force by about 75% to about 99% on a thermoplastic surface coated with the coating formulation as compared to the thermoplastic surface prior to being coated with the coating formulation.

14. The coating formulation of claim 1, which reduces the maximum dynamic friction force by about 90% to about 99% on a thermoplastic surface coated with the coating formulation as compared to the thermoplastic surface prior to being coated with the coating formulation.

15. The coating formulation of claim 1, wherein the copolymer has a molecular weight between about 25,000 g/mole to about 100,000 g/mole.

16. The coating formulation of claim 1, wherein the hydrophilic polymer has a molecular weight between about 1,000 amu to about 40,000 amu.

17. The coating formulation of claim 1, wherein the top coat includes a reaction product of a mixture including a polyethylene glycol di-acrylate having a molecular weight of about 4,000 g/mole, a surfactant, benzophenone, and 1-hydroxycyclohexyl phenyl ketone.

18. The coating formulation of claim 1, wherein the top coat includes a reaction product of a mixture including a polyethylene glycol acrylate having a molecular weight of about 20,000 g/mole, a surfactant, benzophenone, and 1-hydroxycyclohexyl phenyl ketone.

19. A coating formulation comprising:
   a base coat including a copolymer of a first tetrahydrofurfuryl acrylate monomer and a second monomer including a functional group amenable to further derivatization and a plurality of reactive moieties, and
   a top coat including a hydrophilic polymer containing less than two reactive moieties per molecule,
   wherein the hydrophilic polymer has a molecular weight between about 1,000 amu to about 40,000 amu, and
   wherein the coating formulation reduces the maximum dynamic friction force by about 50% or more on a surface coated with the coating formulation as compared to the surface prior to being coated with the coating formulation.

* * * * *